(12) United States Patent
Shoham et al.

(10) Patent No.: US 7,042,564 B2
(45) Date of Patent: May 9, 2006

(54) WAFER INSPECTION METHODS AND AN OPTICAL INSPECTION TOOL

(75) Inventors: Doron Shoham, Rehovot (IL); Oren Reches, Zoran (IL)

(73) Assignee: Applied Materials, Israel, Ltd., Rehovot (IL)

( * ) Notice: Subject to any disclaimer, the term of this patent is extended or adjusted under 35 U.S.C. 154(b) by 136 days.

(21) Appl. No.: 10/215,523

(22) Filed: Aug. 8, 2002

(65) Prior Publication Data

US 2004/0028267 A1     Feb. 12, 2004

(51) Int. Cl.
G01N 21/00 (2006.01)
G01N 21/55 (2006.01)
H01L 21/00 (2006.01)
H01L 21/66 (2006.01)
G06K 9/00 (2006.01)

(52) U.S. Cl. .............. 356/237.2; 356/237.1; 356/445; 438/7; 438/16; 382/141; 382/145

(58) Field of Classification Search .. 356/237.2–237.5, 356/445; 438/16; 156/345.13; 216/60
See application file for complete search history.

(56) References Cited

U.S. PATENT DOCUMENTS

| | | | |
|---|---|---|---|
| 5,909,276 A * | 6/1999 | Kinney et al. ........... 356/237.2 |
| 6,040,912 A * | 3/2000 | Zika et al. .................. 356/394 |
| 6,049,220 A * | 4/2000 | Borden et al. .............. 324/765 |
| 6,165,050 A * | 12/2000 | Ban et al. ....................... 451/8 |
| 6,324,298 B1 * | 11/2001 | O'Dell et al. ............... 382/149 |
| 6,340,602 B1 * | 1/2002 | Johnson et al. ................ 438/7 |
| 6,361,646 B1 * | 3/2002 | Bibby et al. ................... 216/85 |
| 6,574,359 B1 * | 6/2003 | Hance ......................... 382/149 |
| 2002/0142498 A1 * | 10/2002 | Kubota et al. ................ 438/16 |
| 2002/0159626 A1 * | 10/2002 | Shiomi et al. .............. 382/145 |
| 2003/0045100 A1 * | 3/2003 | Saka et al. .................. 438/689 |
| 2003/0219962 A1 * | 11/2003 | Hofmann et al. ........... 438/489 |

\* cited by examiner

*Primary Examiner*—Gregory Toatley, Jr.
*Assistant Examiner*—Gordon J. Stock, Jr.
(74) *Attorney, Agent, or Firm*—McDermott, Will & Emery

(57) ABSTRACT

A method of inspecting a plurality of wafers in an optical inspection tool. The method includes the steps of generating a reference wafer and polishing the reference wafer in a chemical mechanical polishing process following a metal deposition process such that the reference wafer is representative of a fully polished wafer. The optical inspection tool scans the reference wafer and a gray level map is generated. A number of further wafers are metalized, polished, scanned and gray level maps generated. The method includes the step of comparing a gray level map of the scanned reference wafer to a number of gray level maps of the scanned wafers. A determination (314) is then made as to whether the wafer exhibits an acceptable polishing quality based on the comparison.

43 Claims, 10 Drawing Sheets

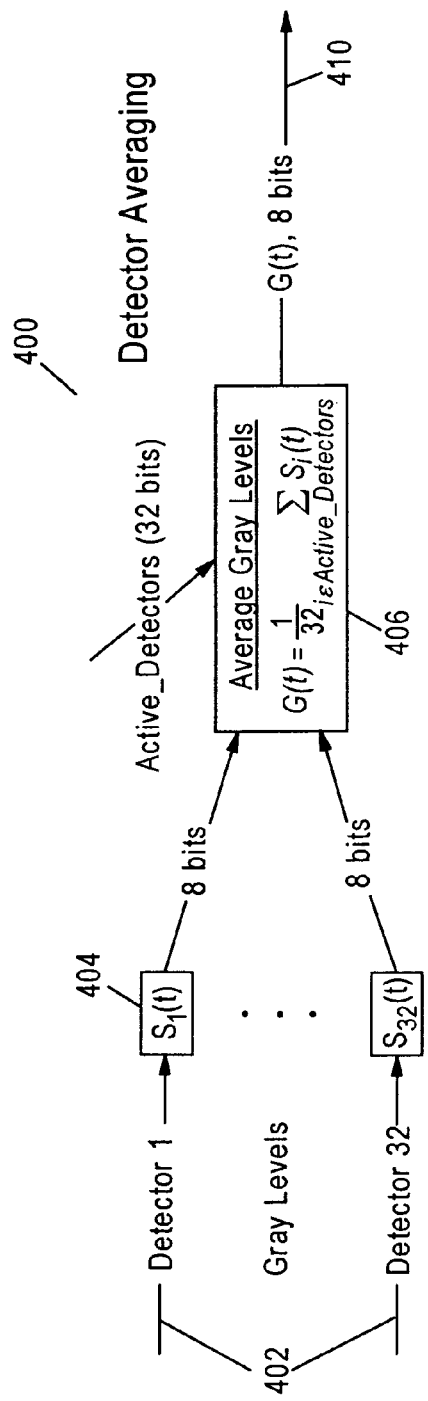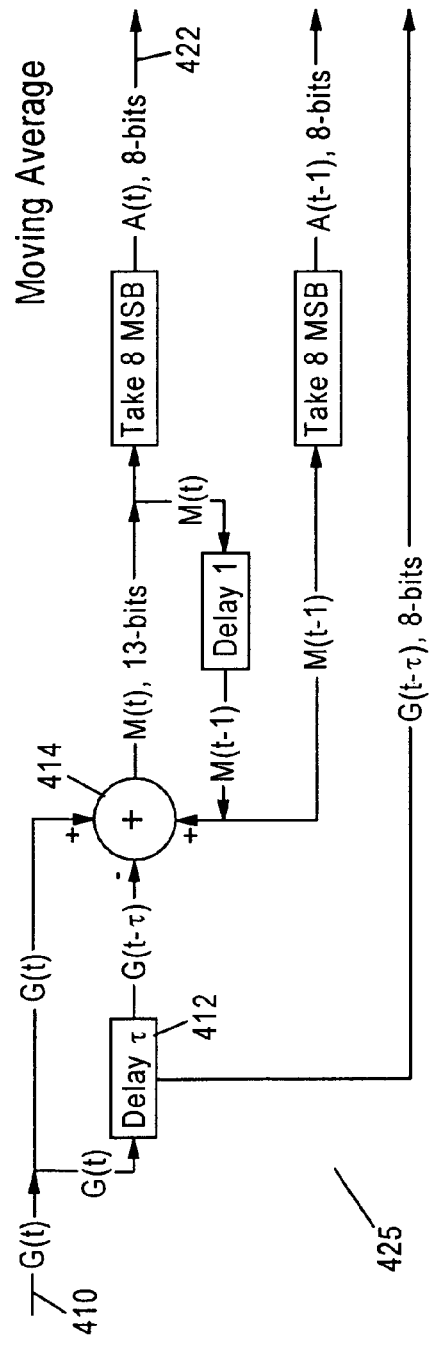

WAFER INSPECTION METHODS AND AN OPTICAL INSPECTION TOOL

FIELD OF THE INVENTION

This invention relates to methods and apparatus for inspecting a semiconductor wafer. The invention is applicable to, but not limited to, automated inspection of semiconductor wafers to detect metal residue after a chemical-mechanical polishing process, using wafer mapping.

BACKGROUND OF THE INVENTION

The use of semiconductor technology has, over the last few decades, revolutionized the use of electrical and electronic goods. In particular, the increased use of semiconductor technology has resulted from an unappeasable need by business (as well as individuals) for better, smaller, faster and more reliable electronic goods.

The semiconductor manufacturers have therefore needed to make commensurate improvements in product quality, as well as in the speed, quality and reliability of the semiconductor manufacturing process. Clearly, in the mass-manufacture of semiconductors, the manufacturer needs to minimize the number of faulty semiconductors that are manufactured. Furthermore, the manufacturer clearly needs to recognize, as early as possible in the manufacturing process, when faulty semiconductors are being manufactured, so that the manufacturing process can be checked and, if appropriate, corrected.

A semiconductor wafer typically includes multi-layer integrated circuits (ICs) that include multiple oxide (insulating) layers and metal (conducting) layers. Horizontal layers are connected to each other by vertical contacts (connecting the first metal layer to the substrate and additional layers that include the transistors themselves) or by vertical vias (connecting conductors of two distinct metal layers). As each metal layer is separated from another layer by an oxide layer (that may also include conductive patterns) the vias/contacts are generated by three steps:
  (i) Drilling vertical holes through the oxide layer,
  (ii) Performing metal deposition that results in filling the vias/contacts but also results in residue metal, and
  (iii) Polishing the oxide layer such that the residue metal disappears.

Many ICs have multiple metal layers, thus the three-step via/contact generation process is repeated many times.

By continuously inspecting semiconductor wafers throughout the manufacturing process, flawed wafers may be removed and, if appropriate, the wafer or wafer manufacturing process corrected at any of the various steps. A wafer inspection may therefore occur after each via/contact generation process. This is much more preferable than completing the whole wafer manufacturing process, only to find that a defect in a wafer, an IC, a via or a layer exists in a final inspection, or by failure during use.

In the field of this invention, the use of automatic defect characterization (ADC) is known in wafer inspection techniques. U.S. Pat. No. 5,808,735 by Lee et al. describes a method for detecting and characterizing defects on a test surface of a semiconductor wafer using a pixel comparison technique between a specially prepared reference blank wafer, and the blank wafers.

European patent application EP 0869352A, from the same applicant as the present invention, describes a further technique for detecting metallic contaminants in a sub-micron semiconductor wafer by comparing a reference (pre-annealed) wafer with an annealed wafer. Such an inspection technique teaches the comparison of a pre-process (reference) wafer with a post-process wafer to determine particle defects, metallic contaminants etc. introduced during the process. A further example of a reference wafer technique, as commonly employed in the field of wafer inspection, is described in U.S. Pat. No. 5,870,187 by Uritsky et al., whereby wafer scanning is used to (i) align wafer surface scan maps, and (ii) locating particle contamination defects, for comparison purposes between a 'before' and 'after' wafer handling or processing operation.

As previously indicated, after the manufacturing process, particularly in the production of ultra-high density integrated circuits, chemical-mechanical polishing (CMP) processes are used to remove material from the surfaces of wafers. CMP processes typically remove either conductive materials or insulative materials from the surface of the wafer to produce a flat, uniform surface upon which, if desired, additional layers of devices may be fabricated.

In a typical CMP process, a wafer is pressed against a polishing pad in the presence of slurry under controlled chemical pressure, velocity, and temperature conditions. The slurry solution typically contains small abrasive particles that abrade the surface of the wafer, and chemicals that etch and/or oxidize the surface of the wafer.

The polishing pad is generally a planar pad made from a continuous phase matrix material, such as polyurethane. Thus, when the pad and/or the wafer moves with respect to the other, material is removed from the surface of the wafer by the abrasive particles (mechanical removal) and/or by the chemical (chemical removal) in the slurry.

When a conductive layer is polished from a wafer, the CMP processes must accurately stop polishing the wafer at a desired endpoint. Conductive layers are typically deposited over insulative layers to fill vias or trenches in the insulative layer and to form electrical interconnections between device features on the wafer.

If the CMP process is stopped before the desired endpoint, leading to "under-polishing" of the wafer as it is termed in the art, then any interconnects will not be electrically isolated from one another and shorting may well occur in the circuit. Conversely, if the CMP process is stopped after the desired endpoint, leading to "over-polishing" as it is termed in the art, then interconnects may be completely removed from the wafer. Therefore, to avoid serious defects in a wafer, it is critical that the CMP process is accurately controlled and stopped at the desired endpoint.

It is particularly difficult to determine the endpoint of the CMP process on wafers that have small "critical areas". The critical areas are typically depressions on the surface of the wafer that are the last point on the wafer from which the conductive material is removed by CMP processing.

In the case of metal CMP, which includes tungsten and/or copper metalization of the wafer, the factors contributing to the incomplete removal of the metal range from the incoming metal thickness variation, through the age of the polish consumables, to equipment issues such as interruption in slurry flow or malfunction of the endpoint hardware. The high costs associated with 300 mm manufacturing necessitate a tight control of the metal CMP process in order to minimize the occurrence of residual metal. Residual metal, caused by an incomplete CMP process, adversely impacts the overall product cycle time and, consequently, the production costs.

The inspection of metalized layers has been predominantly left to human visual inspection, in conjunction with microscopic equipment or using laser light-based inspection tools. The visual inspection process is primarily focused to identify if there is any residue metal left on the post CMP wafer. It is known that this stage is a very important review stage in any production environment, as a small amount of residue metal left on the wafer will damage an entire die and lead to a poor yield.

This human visual inspection process is renowned for being inaccurate due to various factors including stress, eye fatigue and boredom of the operator. Complete inspection of the entire polished wafer surface is not possible. Furthermore, it is prone to human judgment and therefore prone to the inconsistencies between different perceptions by different operators as to the significance of a finding. In addition, smaller circuit geometry and higher throughput requirements are exceeding the feasibility of using a microscope for inspection of residual metal for advanced technology nodes. This situation is further complicated in the case of 300 mm wafers, where there is greater than two-fold increase in the inspection surface area compared to a 200 mm wafer. All of which further results in operator stress, eye fatigue, and often lower quality inspection.

A known post-CMP visual inspection process 100, as shown in FIG. 1, involves the stages:

(i) Inspection with naked eye 120 after CMP step 110.

(ii) Review the wafer using, for example, a microscope 140. A reviewer may give feedback on the quality of the wafer, obtained using the microscope, or recommendations to the CMP team. A human decision is then made on the wafer, and if appropriate, the wafer may be returned to the CMP tool for re-polishing if it is deemed "under-polished", or the wafer rejected. Otherwise the polished wafer is passed to the next process stage 150.

The above inspection approach has the significant disadvantage that the process is very time consuming. In addition, the inspection tool used to determine whether any defect exists fails to provide a quantitative measure of the residue metal on the wafer.

A yet further significant disadvantage emanates from there being a delayed feedback of information to the CMP tool, via the Operator.

Thus, there exists a need in the field of the present invention to provide an improved method and apparatus for a post-CMP residual metal inspection process.

SUMMARY

In accordance with a first aspect of the present invention, there is provided a method of inspecting a plurality of wafers in an optical inspection tool, the method including the steps of: generating a reference wafer; polishing said reference wafer in a chemical mechanical polishing process following a metal deposition process such that the reference wafer is representative of a fully polished wafer; scanning said reference wafer into an inspection tool; generating a gray level map for said scanned reference wafer; performing a metal deposition process on a number of wafers; polishing said number of wafers after said metal deposition process in a chemical mechanical polishing process; scanning said number of wafers into an inspection tool; generating a number of gray level maps for one or more of said scanned wafers; comparing said gray level map of said reference wafer with one or more gray level maps of said number of said scanned wafers, and determining whether one or more wafers exhibits an acceptable polishing quality based on said comparison.

In accordance with a second aspect of the present invention, there is provided a method for determining a quality of a polishing process applied to a metal deposited wafer, the method including the steps of: polishing a wafer after a metal deposition process using a chemical mechanical polishing process; scanning said wafer into an inspection tool to create a wafer map; grouping pixels of said scanned wafer into one or more blocks of pixels; scanning a fully polished reference wafer into said inspection tool to create a reference wafer map; grouping pixels of said scanned reference wafer into one or more blocks of pixels; comparing said scanned reference wafer map to a said scanned wafer map on a block-by-block basis; and classifying one or more of said blocks as being either a block of pixels representing a defect in said wafer or a block of pixels representing a fully polished block of pixels, in order to determine whether said polished wafer is of an acceptable quality.

In accordance with a third aspect of the present invention, there is provided an inspection tool, that is adapted to perform the method steps mentioned above.

In accordance with a fourth aspect of the present invention, there is provided a storage medium storing processor-implementable instructions and/or data for controlling a processor to carry out the method mentioned above.

In accordance with a fifth aspect of the present invention, there is provided an optical inspection apparatus for inspecting a plurality of wafers, the apparatus including: means for receiving a number of metalized wafers polished in a chemical mechanical polishing process; an optical head, operably coupled to the means for receiving, including a plurality of optical detectors for scanning said number of polished wafers including at least one fully-polished reference wafer; a processor, operably coupled to said optical head, for receiving and processing scanning information from said optical head, wherein said scanning information corresponds to said fully-polished reference wafer and one or more polished wafers; and a memory element, operably coupled to said processor for storing said scanning information relating to said fully polished reference wafer; wherein said processor generates a gray level map for said fully-polished reference wafer and one or more polished wafers and compares said gray level map relating to said scanned fully-polished reference wafer to said gray level map relating to at least one scanned polished wafer to determine whether said at least one polished wafer exhibits an acceptable polishing quality based on said comparison.

Further aspects of the invention are as claimed in the dependent claims.

In summary, the present invention provides methods and an apparatus for the automatic optical inspection of a wafer, to identify any residue metal left on the wafer following a polishing process in a CMP tool.

In particular, a method of inspecting a plurality of wafers in an optical inspection tool is described. A number of gray level maps are generated for one or more post-metallization and post CMP scanned wafers and a similarly generated reference wafer. The gray level map of the reference wafer is compared with one or more gray level maps of the number of scanned wafers, in order to determine whether one or more wafers exhibits an acceptable polishing quality based on the comparison. In this manner, by use of wafer maps being compared to a reference wafer map, an assessment of the quality of a CMP process can be quickly determined.

Furthermore, a method for determining a quality of a polishing process applied to a metal deposited wafer is described using a 'macro' level inspection process. The macro level process groups of pixels of a scanned wafer into one or more blocks of pixels and compares the pixel group to a reference wafer pixel group, in order to determine whether the polished wafer is of an acceptable quality. In this manner, the inspection process can be performed even faster, and any defects detected earlier.

Figure 1:
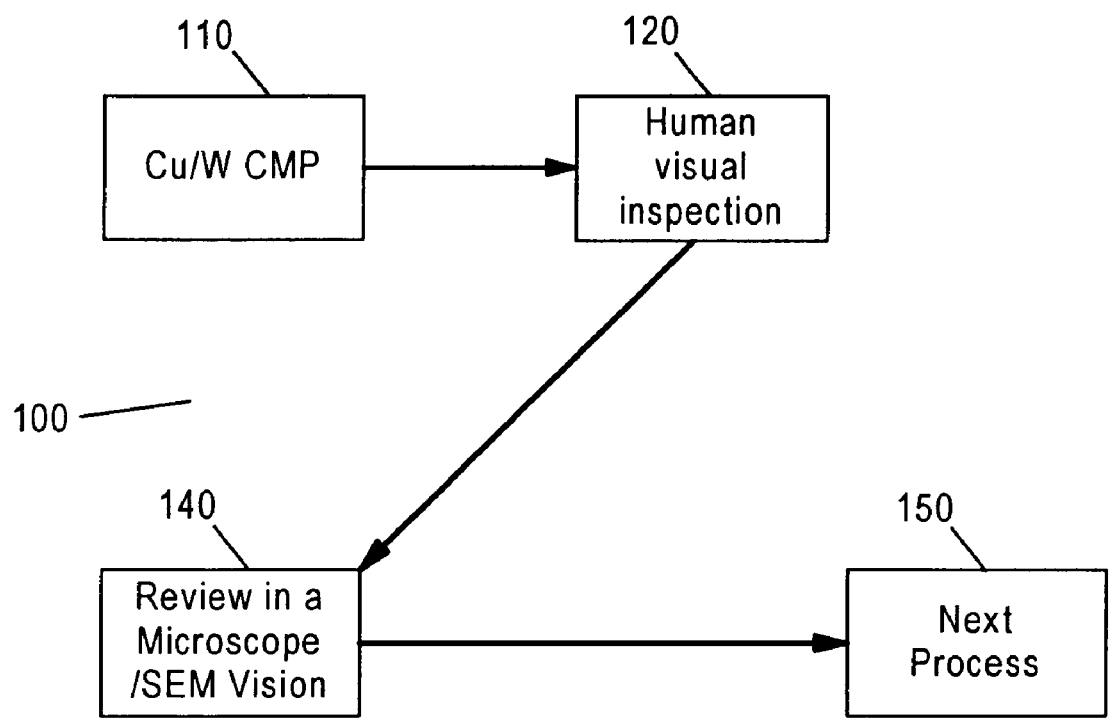
FIG. 1 illustrates a known visual inspection process used following a chemical-mechanical polishing process.
Figure 2:
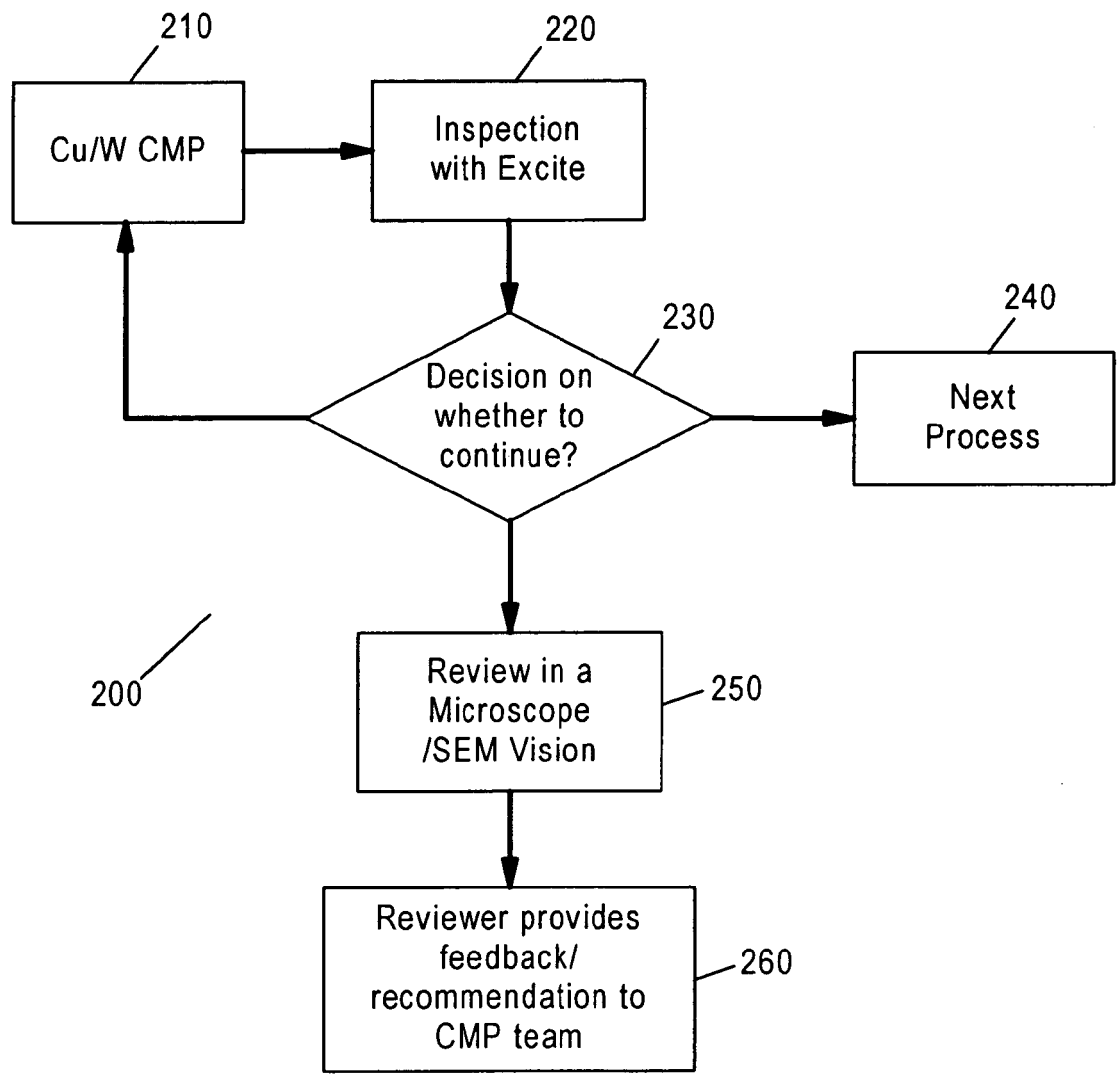

Exemplary embodiments of the present invention will now be described, with reference to the accompanying drawings, in which:

FIG. 2 illustrates an automatic post chemical-mechanical polishing inspection process adapted in accordance with the preferred embodiment of the present invention.

Figure 3A:
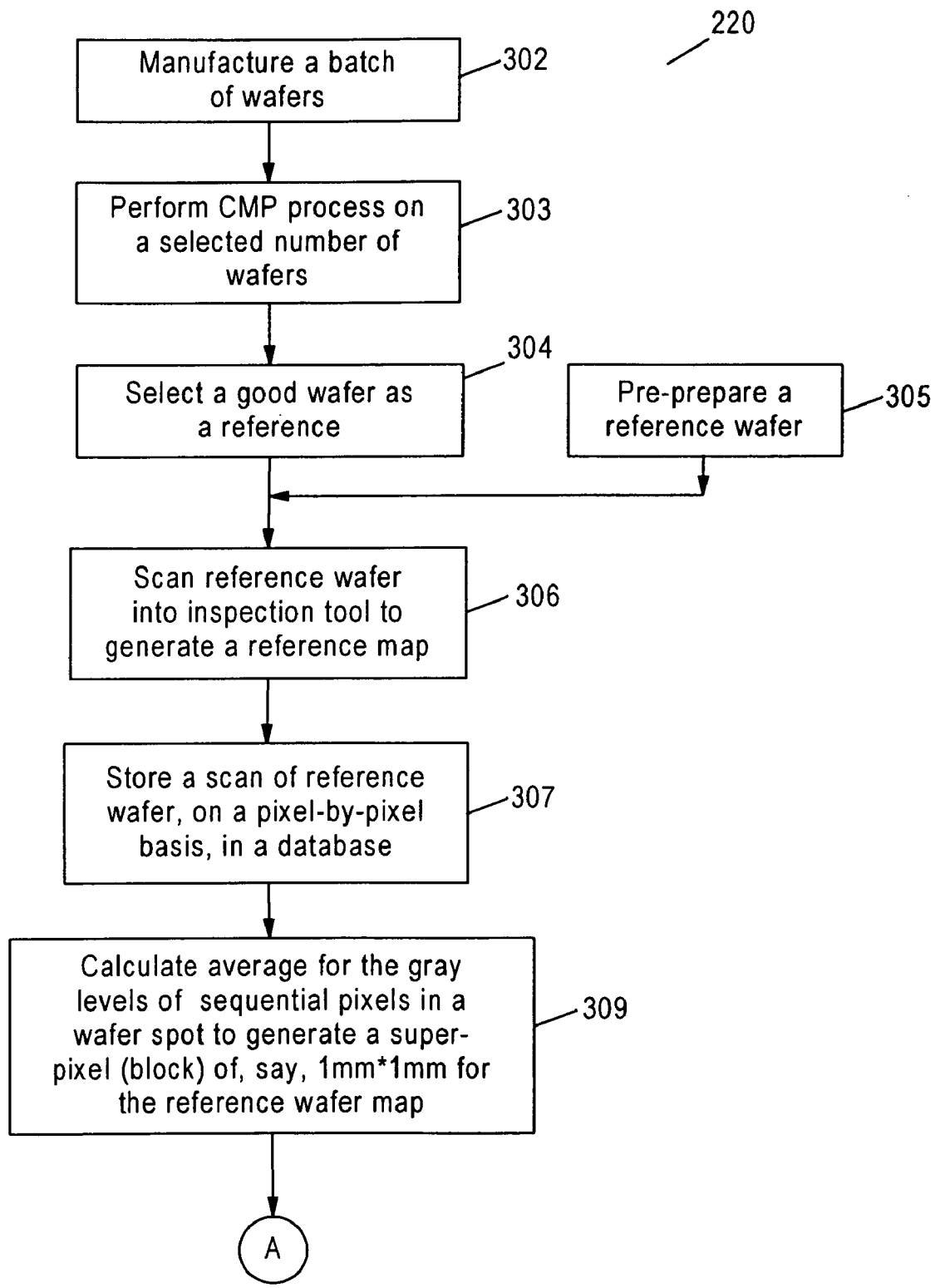
Figure 3B:
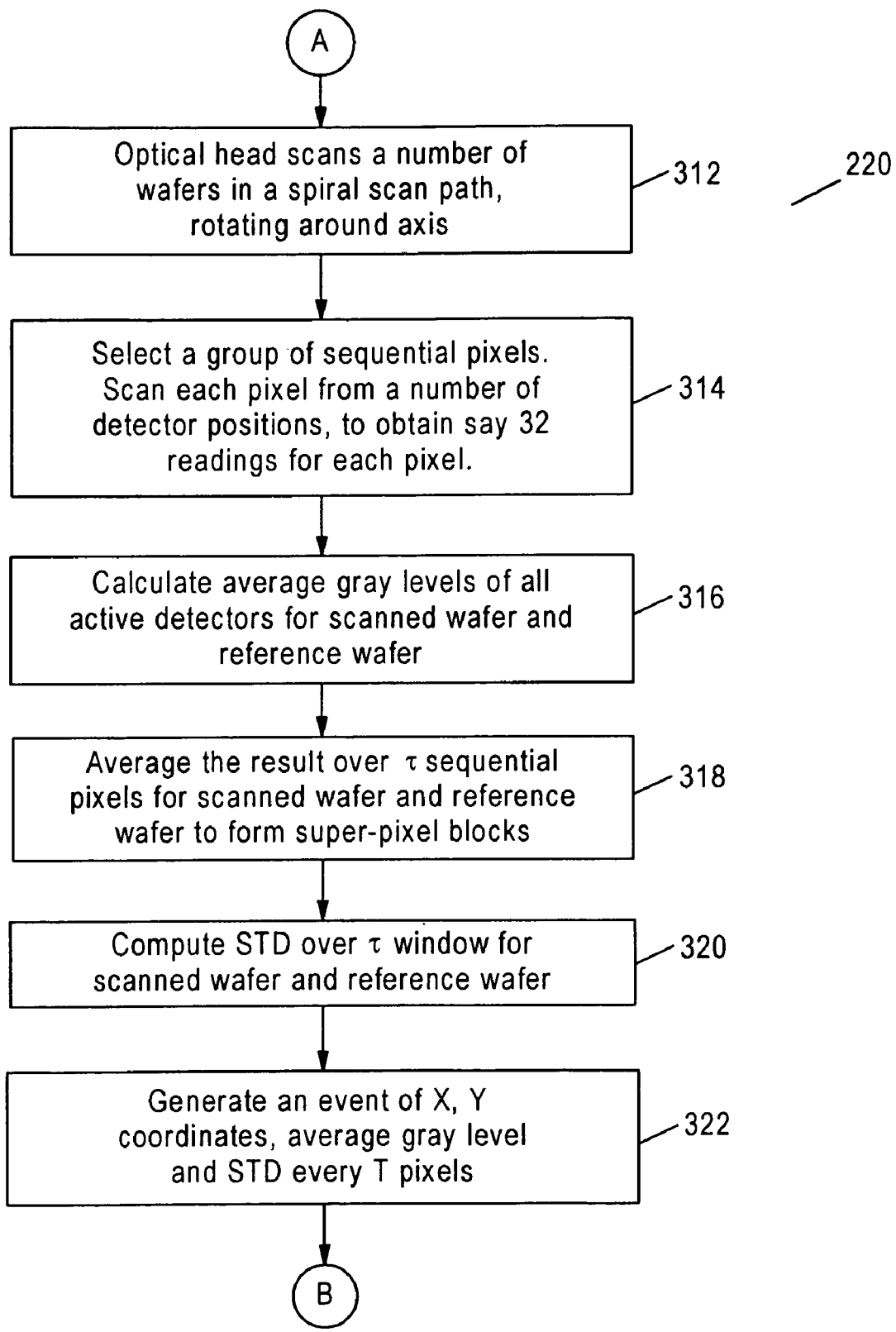
Figure 3C:
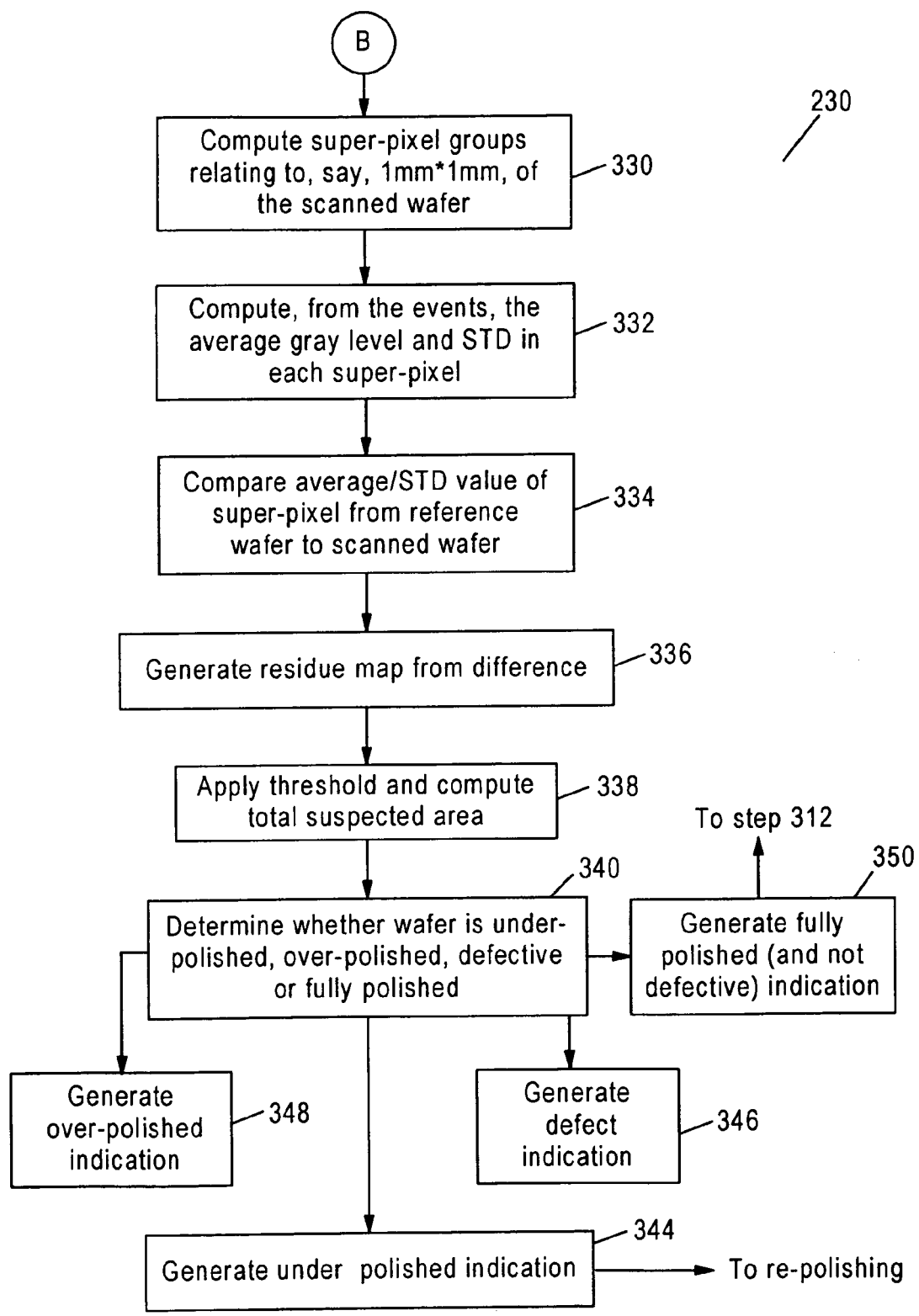

FIGS. 3a–3c shows a flowchart illustrating the wafer inspection method in accordance with the preferred embodiment of the present invention.

FIGS. 4a–4d show a series of analysis steps applied to the data obtained from inspecting wafers, in accordance with the preferred embodiment of the present invention.

Figure 5:
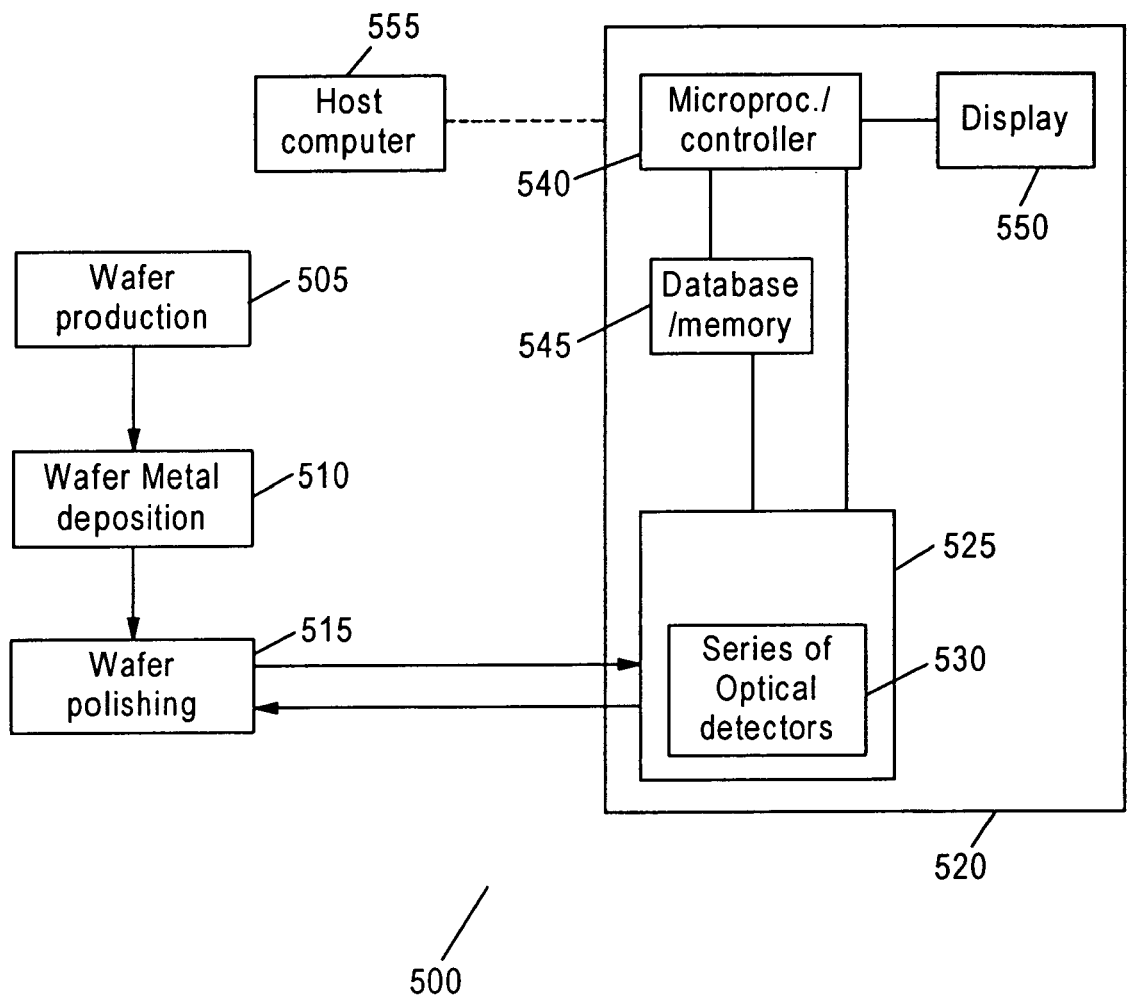

FIG. 5 shows an inspection tool adapted to inspect wafers in accordance with the preferred embodiment of the present invention.

FIGS. 6a–6d illustrate a series of results relating to metal residue inspection, obtained by employing the inventive concepts of the preferred embodiment of the present invention.

DESCRIPTION OF PREFERRED EMBODIMENTS

In the context of the following description, the term 'wafer' is used to encompass any semiconductor device, including bare wafers, patterned wafers, sawn wafers, whole wafers, multi-chip modules, etc.

In summary, the preferred embodiment of the present invention, describes an inspection tool, for example an Integrated Particle Monitor (IPM) tool, which is capable of measuring metal residue on both bare and patterned wafers. This is a new and unique application for post-metal CMP residue metal detection, which replaces the known microscope visual inspection process. The tool uses a previously scanned fully polished 'golden wafer'. The 'golden wafer', in effect, is used as a reference wafer for a given pattern density and metal thickness. The reference wafer is then used to inspect other similarly processed wafers. The tool preferably uses a pixel map for each particular layer of each product/wafer set that is scanned. Advantageously, this technique can be integrated to a CMP process tool, which can lead to a significant reduction in cycle time and improved inspection efficiency.

When wafers of the same product and layer are scanned, each gray level map that is created is compared to a reference wafer map for a particular layer of a particular product. The comparison of the gray level map of the manufactured wafer with the gray level map of the reference wafer is preferably used to produce a residual metal map. The difference in the gray levels is used to provide a measure of the residual metal present on the inspection wafers. Groups of pixels of an inspected wafer map are then combined to form a block of pixels (i.e. a super-pixel). The blocks are then compared with the corresponding blocks of the reference wafer to ascertain whether the block is either one with a metal residue (and thereby under-polished) or one that is fully polished. The determination is preferably made based upon whether a residual metal measurement exceeds a threshold value.

In this manner, the method provides a single-step, fully automated full wafer inspection, with a fast inspection time and high resolution of the inspected wafer. In particular, the inspection tool can also provide a quick (approaching instant) feedback to the CMP polishing tool, so that any problems in the polishing process can be addressed quickly.

The preferred embodiment of the present invention describes the detection of metal residue on wafers after a metal CMP process. The first inventor of the present invention discovered that under polished wafers (i.e. those that include too much metal residue) and over polished wafers are characterized by different brightness than respective areas of fully polished wafers. In some cases the under polished areas are brighter than the respective fully polished areas. The reflection/scattering patterns of under polished and even over polished areas differ then those of fully polished areas, thus enable to detect these areas when using either dark field detection schemes, gray field detection schemes and/or bright field detection schemes.

The first inventor of the present invention also noted that over-polished wafers are difficult to detect, as the oxide layer just gets slimmer. Nevertheless, in some cases, over polished wafers were detected by the first inventor, even when the oxide layer was not completely polished (thus disclosing a lower layer). The second inventor of the present invention noted that the detection of under polishing and especially the detection of over-polishing can be enhanced by employing variable test patterns (holes filled with metal) in the wafer scanning process. A preferred example of such a test pattern includes one having a conical shape, or other shape that has a cross section that changes as a function of the vertical distance from the oxide layer surface. Accordingly, under polishing or over polishing of the test structures (or portions of the test structures) results in distinct cross sections, thus effecting the reflection pattern.

The detection algorithm is further explained with regard to the flowchart of FIG. 3. In particular, in the preferred embodiment of the present invention, the Excite inspection tool scans the wafer along a spiral scan path. The gray levels of several successive wafer areas (spots), preferably from a number of detectors positioned within the Excite tool, are averaged. Preferably, a standard deviation (STD) of the successive wafer areas (spots) is also computed. The location of the central spot out of the succession, the average and preferably the STD are stored in a database for subsequent use.

After the scanning operation is complete, the surface of the wafer is mapped to multiple blocks of pixels, each of about 1 mm$^2$. For example, a 300 mm wafer would include about 90,000 macro pixels of 1 mm$^2$. The average (and STD) of each succession of spots that belong to a block (also referred to as a super-pixel) are processed to provide a single block characteristic. An example of such a characteristic is a function that reflects the intensity (gray level value) of the spots, such as a statistical function, including an average function and/or a STD function applied to the intensity of spots of the same block.

During the comparison stage the characteristic obtained from a block on the reference (fully-polished) wafer is compared to the same characteristic of the corresponding block of the scanned wafer. The absolute value of the result is selected as a parameter to indicate whether or not a defect exists in the polished wafer, and thereby an indication of the quality of the CMP process.

Advantageously, the polishing machine is configured to include a set of concentric polishing rings. In this manner, once the location of one or more defects in an under-polished wafer has been detected, the polishing tool is able to select whether particular rings, out of the set of rings, are to be used in a re-polishing process, for that particular wafer.

In the preferred embodiment, computations are made by a host computer, for example with one or more dedicated signal processing cards being inserted within the Excite inspection tool.

Thus, the first inventor of the present invention has developed an algorithm, as further described below, aimed at detecting regional changes in a gray level scan of a wafer being inspected, when compared to a fully-polished reference wafer. In addition, the first inventor of the present invention has also proposed that the analysis tool also looks at regional changes of a measured standard deviation (STD) of the gray levels.

In particular, the proposed algorithm includes learning a coarse map of gray levels (and STD) over the whole reference ("golden") wafer as part of a 'recipe' generation process to implement a "Macro" inspection mode. During inspection, a similar map of the scanned wafer is generated. Any area detected as exhibiting a significant change from the corresponding reference wafer area is marked as under-polished. The averaging needed to compute these maps is preferably performed in two steps.

The first step, preferably performed on a card in the host computer that is operably coupled to the inspection tool, is to average inspection measurements over a number of detectors and over sequential pixels.

The second step, also performed on the host computer, is to average the inspection measurements over a larger block area—creating a "super-pixel" to be used in a comparison step at a 'Macro' inspection level. The comparison of the observed map to the reference map is also performed on the host. The results are preferably presented in both a graphical and numerical format.

Referring now to FIG. 2, a post-CMP visual inspection process 200 is described, in accordance with the preferred embodiment of the present invention. The stages of the improved process include, as in the prior art process, performing a chemical-mechanical polishing process after depositing a layer with copper (Cu) or Tungsten (W) metalization 210. Of note is that the wafer inspection process is then performed automatically using an improved inspection tool 220, in contrast to a human visual inspection.

The automatic inspection process is further described with respect to FIG. 3A and FIG. 3B. After the reference wafer has been compared to a number (preferably all) of the manufactured and polished wafers, a decision is made as to how to deal with each respective inspected wafer 230. The decision process, and any subsequent course of action, is further described with respect to FIG. 3C. Another wafer is then selected for inspection, or a new batch of wafers is selected for manufacturing, metal deposition and polishing 240.

It is within the contemplation of the invention that particular wafers may be further analyzed using a microscope or SEM vision tool 250. If appropriate, the results of the further analysis of the wafer may be fed back to the CMP team, so that the polishing process can be adapted in response to the analysis, or the wafer re-polished 260.

Referring now to FIGS. 3A to 3C, a new method of inspecting wafers 220 is described using a "Macro" level inspection process, in accordance with the preferred embodiment of the present invention. The preferred method may be initiated each time a batch of wafers is manufactured, as shown in step 302. A chemical-mechanical polishing (CMP) process is then performed on the manufactured (and metal deposited) wafers, as in step 303.

In the residue metal inspection mode, the tool is first configured to recognise a pixel configuration of a fully polished (reference) wafer. Advantageously, the reference wafer is preferably selected from the initial batch of wafers, as the wafer that best represents optimal polishing, as shown in step 304, in order to reduce the impact on the manufacturing process cycle time. Furthermore, the selection of a reference wafer from a particular batch of wafers being manufactured is more representative of the polishing quality required of the wafer batch.

In an alternative embodiment, a specifically manufactured and polished wafer may be produced, purely to be used as an 'ideal' reference wafer, as in step 305.

In accordance with the preferred embodiment of the present invention, the inspection tool scans the whole of the fully polished reference wafer to generate a reference wafer map, as shown in step 306. The scan of the reference wafer is preferably stored on a pixel-by-pixel basis, as shown in step 307.

Notably, the preferred embodiment utilizes a succession of reduced scan areas, for example: using an edge exclusion of 1000µ (instead of 3000µ), a center exclusion of 300µ (instead of 1000µ), a phi pixel of 6µ (instead of 3µ), and a theta pixel of 100µ (instead of 25µ). The use of such criteria and values differs from the known technique for scanning patterns, as will be understood by those skilled in the art. Values for the three scanning speeds are preferably set as follows. In the preferred embodiment, the theta pixel is configured as: 100µ, 300µ, and 1000µ for sensitive, fast, and ultra-fast scanning speeds respectively. Also, for the phi pixel, a 6µ scanning speed is set for all speeds, with the default speed preferably set as "sensitive".

Having obtained pixel information relating to the whole reference wafer, the inspection tool then averages the gray levels of sequential pixels to generate a super-pixel block of the selected reference wafer, as shown in step 309. In the preferred embodiment of the present invention, the scanned area includes an edge exclusion of (−500µ), a center exclusion of 0µ, a theta pixel of 100µ, and a phi pixel of 6µ.

Once the pixel configuration has been generated on a fully-polished reference wafer for a particular layer of a particular product, the inspection tool is able to scan all polished wafers relating to that layer of that product, as shown in FIG. 3b. In accordance with the preferred embodiment of the present invention, the optical head of the inspection tool scans the polished wafers in a spiral scan path, rotating around an axis, to obtain a clearer view of the wafer spot being inspected, as shown in step 312. Readings from multiple optical detectors are then taken for each pixel, as shown in step 314.

The host computer then groups sets of pixels into blocks (super-pixels), by calculating average gray levels of all the active detectors, so that areas of the wafer can be assessed more easily, as shown in step 316. The calculated average gray level is then averaged over τ sequential pixels, for example for the scanned wafer and the reference wafer, in step 318. The STD is then computed over the same τ time window for the scanned wafer and reference wafer, as in step 320.

However, it should be noted that the reference wafer can be averaged and an STD value calculated at any suitable processing time.

An event is then generated using, for example, the X, Y co-ordinates of the average gray level and STD every T pixels, as shown in step 322.

Referring now to FIG. 3c, the analysis step 230 performed by the host computer is described. The host computer generates super-pixel groups relating to, say, 1 mm*1 mm of the scanned wafer, as shown in step 330. For each super-pixel, the host computer then computes the average gray level and STD from the events, as in step 332. The scanned gray level map (and, if desired, the STD map) is then compared against the average gray level (and STD) map of the corresponding block of the reference wafer, on a block-by-block (super-pixel by super-pixel) basis, as shown in step 334.

It is within the contemplation of the invention that a high-speed processor in the inspection tool, in contrast to the host computer, could perform the same comparison in a real-time manner.

In accordance with the preferred embodiment of the present invention, the comparison of the gray level maps of the scanned wafer to the fully-polished wafer may also be used to produce a new residual metal map, as shown in step 336. The residual metal maps for each of a number (or all) of the scanned wafers, are preferably stored in the host computer.

The residual metal maps may then be accessed when required, as in step 320, to provide an assessment of the quality of polishing of that wafer batch. It is envisaged that the analysis may be performed, using any processor/computer that can accurately and speedily compare the respective maps of super-pixels.

Using the residual metal map the inspection tool is able to report that an individual pixel may be considered as a metal residue or as, say, a fully polished pixel, depending upon a comparison with the corresponding pixel on the reference wafer. It is envisaged that if a block of pixels were deemed to be a metal residue, further analysis of the block could be performed to determine defects at a (micro) 'pixel' level, if desired.

Next, the host computer of the preferred embodiment sets a threshold value and computes a total area of wafer that may be over polished, under polished or defective, in step 338. A value above the threshold indicates that the area may be defective (e.g.—include foreign materials, scratches, over polished or under polished).

Step 338 is followed by a step 340 of determining whether the suspected area is over polished, under polished or defective. Step 340 may be implemented in various ways, such as but not limited to: (a) reviewing the wafer that includes the suspected areas by an automated review apparatus, (b) comparing the results of step 338 to previous results of wafers that were previously determined to be over polished or under polished, or (c) examining test patterns that have a cross section that varies as a function of their height.

Step 340 if followed by steps 344, 346, 348 and 350, if the wafer is found to be under polished, defective, over polished or fully polished, accordingly. Step 348 include generating an over polish indication. Step 346 includes generating a defect indication, that may include additional data regarding the defect. Step 350 included generating a fully polished indication and jumping to step 312 for scanning another wafer. Step 344 includes generating an under polished indication thus allowing the wafer to be re-polished.

The threshold value is preferably stored in the host computer and may be set/selected via the user interface (UI). The UI for this step should also contain a bin size for the "super-pixels", namely the number of pixels used in a block.

It is envisaged that one or more thresholds may be pre-determined or set after the creation of the reference wafer's pixel map. Furthermore, the one or more threshold value(s) may be pre-determined for a particular wafer or semiconductor product, or they may be programmed into the computer as further tests on the manufactured wafers are analyzed. Preferably, the analysis of the inspected wafer information may also be used to vary certain inspection parameters such as resolution, threshold etc. in optimizing the residue metal inspection algorithm. Advantageously, the analysis also enables the coordinates of the residue spots on the wafer to be saved, as well as the residue map(s) to be saved as an individual image(s).

Referring now to FIGS. 4a to 4d, the preferred function of the analysis performs a data reduction algorithm, which includes the following steps:

First, a detector averaging process 400 is shown in FIG. 4a, whereby an average value for the gray levels of a scanned wafer is calculated for all active detectors 402. The detector outputs provide 8-bit gray levels that are input to an averaging function 406. Let us define $S_i(t)$ 404 as the gray level of detector i at time t. Thus, the average of the gray levels 406 may be defined as:

$$G(t) = \frac{1}{32} \sum_{i \in \text{Active\_Detectors}} S_i(t) \qquad [1]$$

It is noteworthy that, for ease of implementation, the sum of gray levels is divided by, say, 32 rather then by the actual number of active detectors. Taking the top 8 bits of a 13-bit sum preferably performs this. The 8-bit signal G(t) 410 may then be input to the next stage.

The next stage is to perform a moving average computation 425 on the 8-bit signal 410 over τ sequential pixels, as described in FIG. 4b. The 8-bit gray level signal G(t) 410 is averaged in time over a window of τ pixels using delay function 412 as shown. It is noteworthy that the preferred embodiment of the present invention takes the 8 most significant bits (MSBs), from say the 13-bit output from the summation 414 of the input signal and the delayed signal. The formal definition of this moving average 422 is:

$$A(t) = \frac{1}{\tau} \sum_{k=t-\tau+1}^{t} G(k) \qquad [2]$$

To simplify the above implementation, it is recommended that the following recursive formula be used to generate the moving average sum:

$$M(t) \equiv \sum_{k=t-\tau+1}^{t} G(k) = M(t-1) + G(t) - G(t-\tau) \qquad [3]$$

With the moving average 422 being defined by:

$$A(t) = \frac{1}{\tau} M(t) \qquad [4]$$

The above formulae provide, for each pixel, the average gray level value of the τ pixels preceding that particular pixel. To obtain the correct phase, the average A(t) should be coupled with the coordinates of the pixel from time t−(τ−1)/2.

Figure 4C:
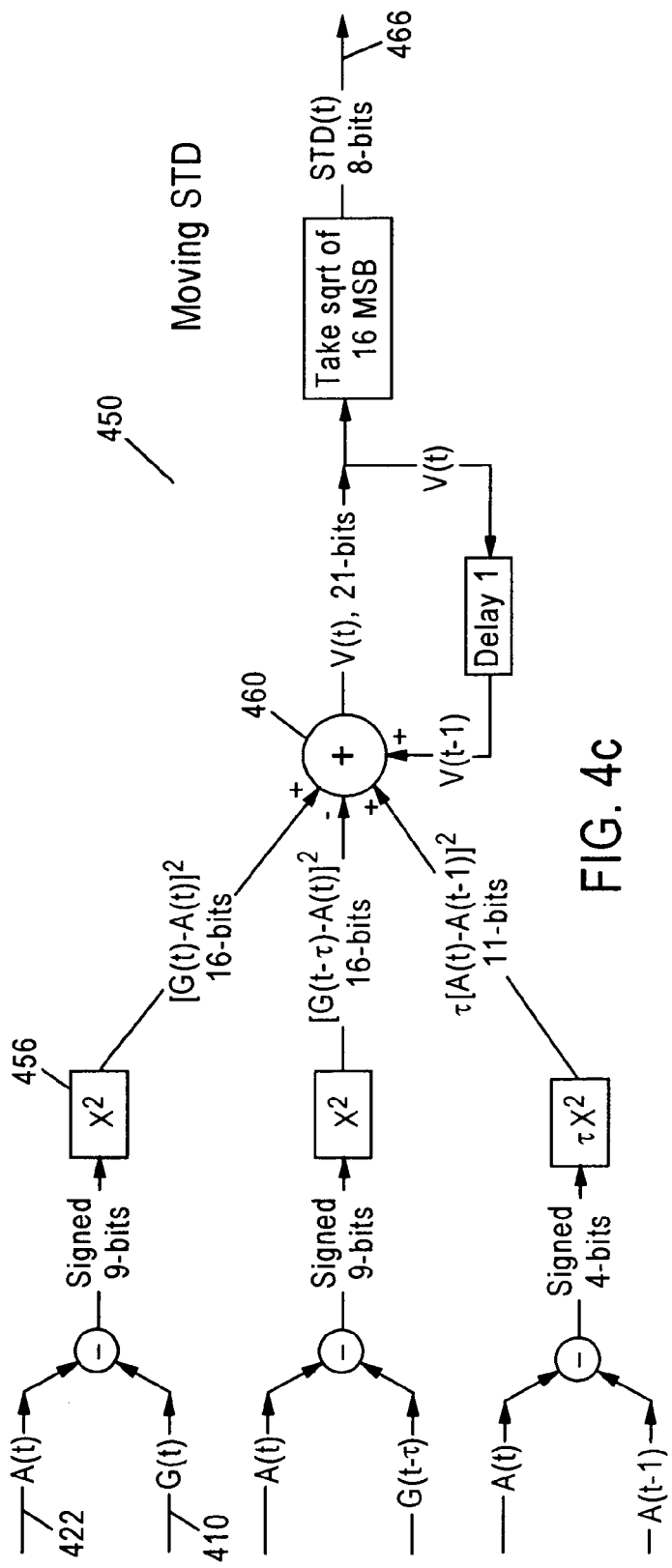

In addition to the moving average, the preferred embodiment also computes the moving standard deviation (STD) 450 of the signal G(t) over the same τ-pixels window, as shown in FIG. 4c. Here, the moving average 422 is subtracted from the 8-bit gray level signal G(t) 410. A signed 9-bit signal is produced for each computation (over time), which is squared in a series of squaring functions 456. The respective squared outputs are then combined in summer 460 as shown. The formal definition of the moving STD is:

$$STD(t) = \sqrt{\frac{1}{\tau} \sum_{k=t-\tau+1}^{t} [G(k) - A(t)]^2} \quad [5]$$

Again, the implementation can be simplified by using the following recursive formula for the moving sum of squares:

$$V(t) \equiv \sum_{k=t-\tau+1}^{t} [G(k) - A(t)]^2 = \quad [6]$$
$$V(t-1) + \tau \cdot [A(t) - A(t-1)]^2 + [G(t) - A(t)]^2 - [G(t-\tau) - A(t)]^2$$

The moving STD is then defined by:

$$STD(t) = \sqrt{V(t)/\tau} \quad [7]$$

Again, to obtain the correct phase, STD(t) should be coupled with the coordinates of the pixel from time t−(τ−1)/2.

Figure 4D:
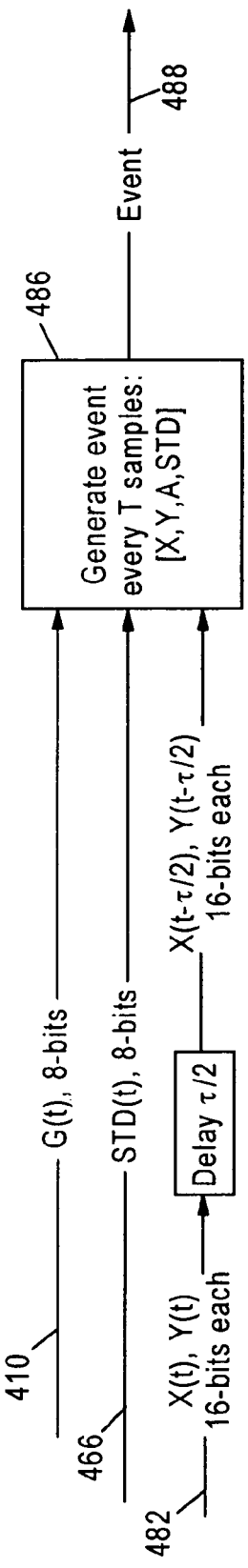

Finally, in accordance with the preferred embodiment of the present invention, an event 488 is generated 486 comprising the super-pixel's X, Y coordinates 482, the average gray level 410, and the local STD 466 every T pixels, as shown in FIG. 4d.

It is envisaged that the UI may be used to specify algorithm parameters in the host computer in the manner shown below in Table 1.

TABLE 1

Algorithm Parameters

| Parameter | Meaning |
|---|---|
| Active_Detectors | Which detectors to include (32-bit word)? |
| τ | Number of pixels to average |
| T | Sub sampling: An event is generated every T pixels |

It is further envisaged that once the host computer has completed the analysis, it may display the generated metal residue map for the scanned wafer to the user/operator, for example to allow further microscopic inspection.

However, it is within the contemplation of the invention that such human interaction may be avoided by making the whole wafer review process automatic. As such, dependent upon the one or more threshold values used, a decision may be made automatically as to whether the scanned wafer is acceptable, is under-polished and requires further polishing, or can be considered as a defective wafer due to over-polishing.

Referring now to FIG. 5, a block diagram of a wafer inspection configuration 500 is described, in accordance with the preferred embodiment of the present invention. A standard wafer manufacturing line is shown, with wafer production 505, followed by a metal deposition process 510, using for example copper or tungsten, and a wafer polishing process 515. The wafer polishing process in the preferred embodiment of the present invention uses a chemical-mechanical polishing (CMP) process.

The polished wafers are input to an Excite™ (EXCursion Inspection TEchnology) inspection tool 520. The inspection task in accordance with the preferred embodiment of the present invention is to find selected areas (ranging from a few mm² to whole wafers) of one or more scanned wafers, which were left under-polished after the CMP process. Notably, the Excite inspection tool together with the host computer 555 performs this application as a 'macro-inspection' task. This is in contrast to known IPM/Excite defect detection applications, which are 'micro-inspection' tasks. The "Macro" inspection operation is achieved by the host computer 555 grouping pixels into blocks (super-pixels) so that they can be more efficiently compared with corresponding blocks of a reference wafer.

The Excite inspection tool performs scanning of polished wafers and the host computer 555 generates a gray level map for each polished wafer. The scanning operation is performed in the optical head 525, which comprises a series of Optical detectors 530. In the preferred embodiment of the present invention, the optical head used for the residue metal inspection has thirty-two detectors. The algorithm to perform and control the inspection of the wafer is preferably stored in memory element (or database) 545, under control of the microprocessor (or controller) function 540.

The first inventor of the present invention have determined that when all the detectors are used equally, to calculate the average gray level across the whole of a wafer, less than optimal results are obtained. Hence, the inspection process of the preferred embodiment of the present invention has been further improved to include a weighting function allocated to individual detectors. The weighting function takes into account the importance of acceptable metal residue at particular locations (scanned by corresponding detectors) of a given wafer.

The host computer performs the following analysis steps, in accordance with the flowchart of FIG. 3c. Events in partial "super-pixels" are removed, in contrast to removal of partial dies, whereas events are removed in drop-dies in a similar manner to that of the existing pattern process. The host computer then generates a grid of "super-pixels", or bins of size Bin_Size×Bin_Size, and computes, from the events, the average gray level and STD in each super-pixel.

At this stage the average gray levels and average local standard deviations (STD) are computed for each bin in the grid. The number of bins along each dimension is given by:

$$N\_Bins = 2*[(Rmax/Bin\_Size)] \quad [8]$$

Where:
Rmax is the outer scan radius (from the recipe for inspection scan.

With each super-pixel three accumulators are preferably used: an event counter N, sum of the mean gray levels M, and sum of the standard deviations S. Each of these accumulators is preferably a two-dimensional matrix of (N_Bins×N_Bins, long integers). The accumulators are also preferably initialized to zero.

For each event E, the three accumulators are increased in the particular super-pixel. Each event E is comprised of the values (X, Y, A, STD), where X, Y are the coordinates, A is the mean gray level and STD is the local standard deviation at these coordinates.

The indices of the bin to be updated may be given by:

$$I = \lfloor (Y/\text{Bin\_Size}) \rfloor + N\_\text{Bins}/2 \quad [9]$$

$$J = \lfloor (X/\text{Bin\_Size}) \rfloor + N\_\text{Bins}/2 \quad [10]$$

Where the indices are in the range [0, N_Bins−1]. This corresponds to wafer coordinates:

$$[-(N\_\text{Bins}/2-\tfrac{1}{2})*\text{Bin\_Size}:\text{Bin\_Size}:(N\_\text{Bins}/2-\tfrac{1}{2})*\text{Bin\_Size}]$$

The accumulators are updated for each event using:

$$N(I, J) = N(I, J) + 1 \quad [11]$$

$$M(I, J) = M(I, J) + A \quad [12]$$

$$S(I, J) = M(I, J) + STD \quad [13]$$

For debug purposes, these accumulators may be saved in a file, with file names indicating: product/layer/recipe/lot/wafer names.

At the end of the scan the averages are computed for all bins and the results normalized for the number of detectors used in the computation:

$$M(I, J) = \begin{cases} \lfloor D \cdot M(I, J)/N(I, J) \rfloor & N(I, J) \neq 0 \\ 255 & N(I, J) = 0 \end{cases} \quad [14]$$

$$S(I, J) = \begin{cases} \lfloor D \cdot S(I, J)/N(I, J) \rfloor & N(I, J) \neq 0 \\ 255 & N(I, J) = 0 \end{cases} \quad [15]$$

$$D = (32/\text{number\_of\_active\_detectors})*(254/255) \quad [16]$$

The normalization factor D compensates for the fact that the results for the super-pixel are divided by '32' instead of by the number of detectors actually used. It is also used to scale the results to [0,254] instead of [0,255]. In this manner, '255' is retained as a marker for non-valid entries, whilst using one byte per pixel.

When learning a new recipe, i.e. a wafer map for a new wafer layer, the host computer saves the arrays in a table (as unsigned-byte arrays) associated with the recipe.

The host computer then compares the residue map for the selected super-pixel to the associated reference wafer map stored in the database. The residue map is preferably computed by taking the absolute value of the difference between the M matrix defined above ($M_{current}$) and the corresponding matrix from the reference wafer ($M_{reference}$). A similar map may be computed from the S matrices.

$$MAP(I, J) = \begin{cases} |M_{current}(I, J) - M_{reference}(I, J)| & M_{current}(I, J) \neq 255 \,\&\, M_{reference}(I, J) \neq 255 \\ 255 & \text{Otherwise} \end{cases} \quad [17]$$

Since the outer radius in the recipe-learning scan (of the reference wafer) may be different from that during a normal inspection mode, the number of pixels inspected may be different. Thus, before computing the residue map, there should be either cropping of the larger matrix, or padding with 255 of the smaller matrix. Any cropping or padding operation is preferably limited to half the difference in number of bins on each side (top, bottom, right, left).

The next step is to threshold the resulting map:

$$MAP(I, J) = \begin{cases} 0 & 0 \leq MAP(I, J) < \text{Sensitivity\_Threshold} \\ MAP(I, J) & \text{Otherwise} \end{cases} \quad [18]$$

A difference is then computed for each super-pixel. Preferably, the host computer then applies one or more thresholds to the difference value in order to determine the polishing performance, for example the total area (in mm$^2$) that has been under-polished, as follows:

$$AREA = \text{Bin\_Size}^2 * \sum_{\{I,J|0<MAP(I,J)<255\}} 1 \quad [19]$$

The results of the automatic determination of polishing performance can then be saved, where the value from equation [19] is the analog calculation of the defect count. The results may also be shown to an operator, to be applied in a re-polishing process, if desired. A preferred example to display results would be to show a color-coded map of the computed differences. The results may additionally be reported to an inspection tool in a substantially real-time manner. A block of pixels may be considered as containing a metal residue, as an under-polished block of pixels, as an over-polished block of pixels, or as a fully polished block of pixels, such that a polishing process can be adapted in a substantially real-time manner.

TABLE 2

| Algorithm Parameters | |
|---|---|
| Parameter | Meaning |
| Bin_Size | Size (in mm) of bins for gray level averaging |
| Sensitivity_Threshold | Minimal gray-level difference to present |

The host computer 555 is operably coupled to the modified Excite inspection tool 520 in an alternative embodiment in order to receive the raw inspection data, thereby (potentially) increasing the speed of residue metal inspection analysis. The host computer 555 reduces the raw data into a gray level map for each wafer and compares each inspected wafer with the reference wafer to generate a corresponding metal residue map, as described.

A human visual inspection of the residue maps of the scanned wafers, created following comparison with the reference wafer may then be performed, by presenting the wafer map images on a display 550. Examples of such residue maps from the inspection tool 520 were compared in human visual tests. On a qualitative basis the inspection tool residue map was found to match exactly with the human visual inspection. A further review was performed on the scanned wafers, using a microscope, which confirmed that the residue spots identified by the inspection tool were indeed accurate.

The various components within the inspection tool are realised in this embodiment in an integrated component form. Of course, in other embodiments, they may be realized in discrete form, or a mixture of integrated components and discrete components, or indeed any other suitable form.

Furthermore, in this embodiment the host computer 555 or internal image processor function is implemented preferably in a digital signal processor. However, it is within the contemplation of the invention that the inspection algorithm and/or any associated threshold levels as described in the above embodiments may be embodied in any suitable form of software, firmware or hardware.

The inspection tool may be controlled by processor-implementable instructions and/or data, for carrying out the methods and processes described, which are stored in a storage medium or memory, for example the memory element 545. The processor-implementable instructions and/or data may include one or more of the following:

(i) The inspection algorithm itself, to control the scanning and comparison steps,
(ii) A new reference wafer map, should a specifically designed reference wafer be used,
(iii) A new threshold level, to dictate whether the scanned wafer should be deemed polished and passed, deemed under-polished and need re-polishing, or deemed over-polished and therefore defective,
(iv) Information relating to the product, wafer type or layer of a wafer that is being inspected.

The memory element 545 may be a circuit component or module, for example a random access memory (RAM) or programmable read only memory (PROM), or a removable storage medium such as a disk, or any other suitable medium.

The first inventor of the present invention has been able to validate and quantify the benefits of the inventive concepts for various metallic elements, for example copper (Cu) and Tungsten (W), deposited on wafers. A variety of wafers, ranging from fully polished to very severely under polished post WCMP wafers, were scanned using the inspection tool. For each of the test wafers a residue map was generated.

During the process of learning a recipe or table for a particular wafer, it is preferable that the events and sum of gray levels (providing an average gray level) for each super-pixel are stored in the database as part of the recipe. For areas outside the wafer, a "no data" indication may be used. Subsequently, when executing the known recipe, a table of differences between the known (reference) gray level distribution and the new gray level distribution may be generated.

It is proposed to store this tabular result in a custom-made binary format. The file preferably consists of header, an array of gray level averages, and a summary. The header preferably contains identification data (such as date, wafer type (product/layer/recipe), wafer size, die geometry (center, offset, dies list), resolution (number of super-pixels), type of contents (gray levels or difference between gray levels)). The summary preferably contains numeric characteristics of the result, analogous to a defects count for a usual scan. It is also envisaged that the same format will be used for each recipe table and results table. The format should support easy extension thereto, for example by containing a tag for each field, or maintaining offsets to important areas.

In the preferred embodiment, the result is displayed as a color-coded map. In this context, 25 to 50 color ranges are defined and each super-pixel is drawn with a corresponding color. A wafer contour and a die map are also displayed in the usual manner as a defect map. When a cursor passes over the map, coordinates of the point and corresponding gray level value are preferably displayed in the legend area of the map. The legend may also preferably contain a slider operation, thereby enabling easy switching of minimal and maximal gray levels to the display.

Figure 6A:
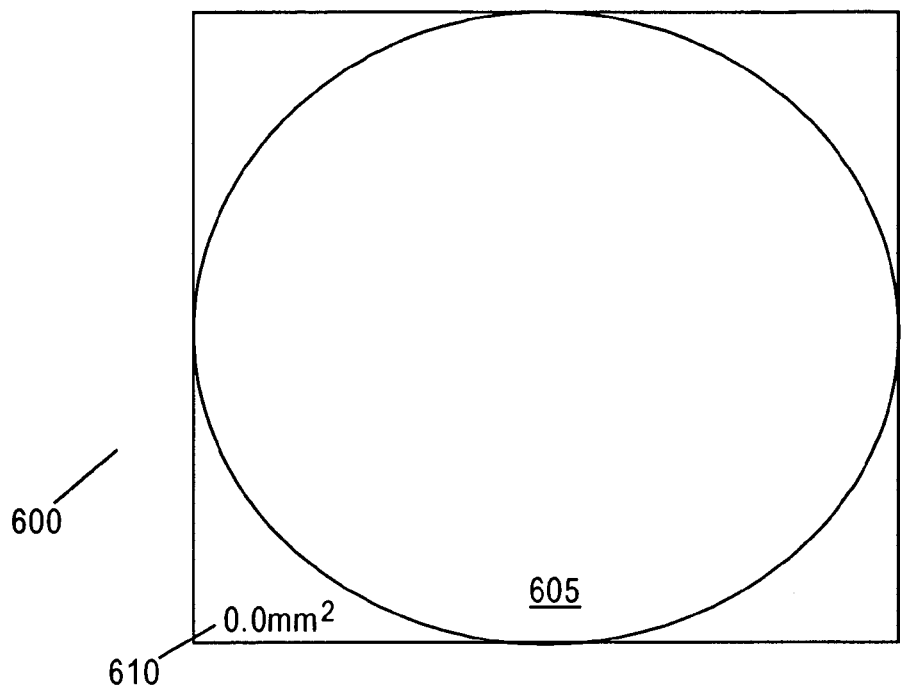
Figure 6B:
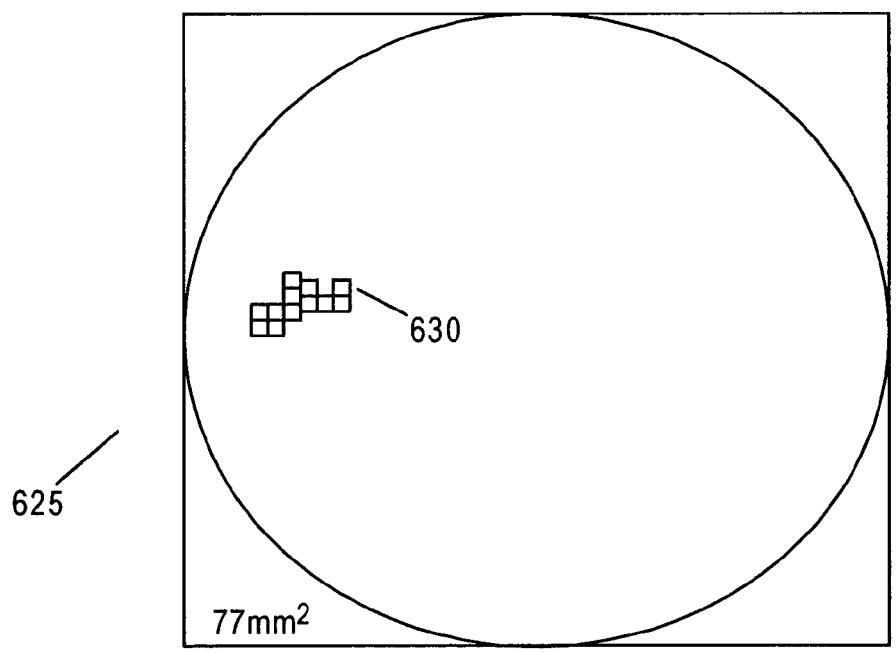
Figure 6C:
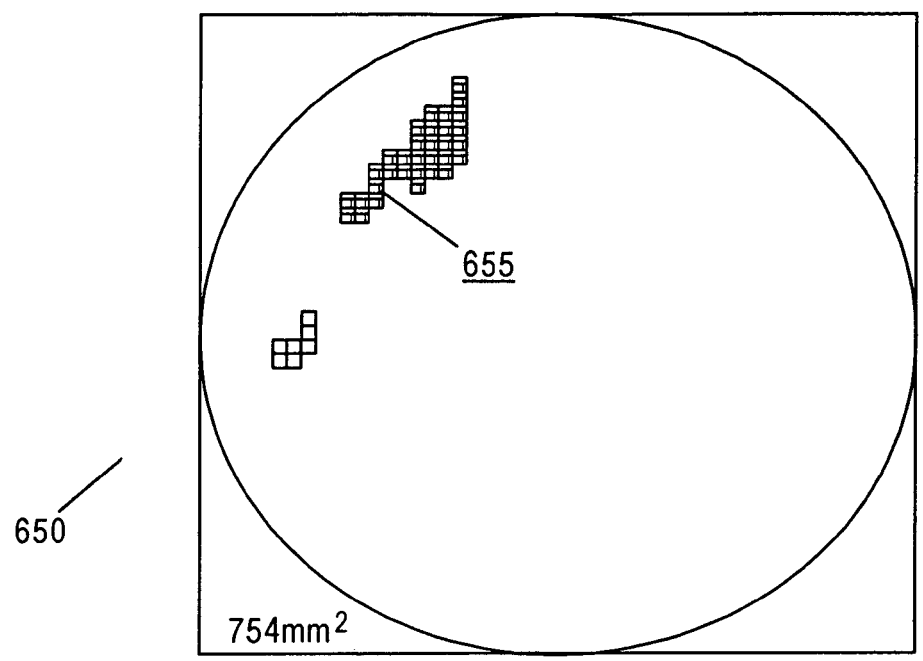
Figure 6D:
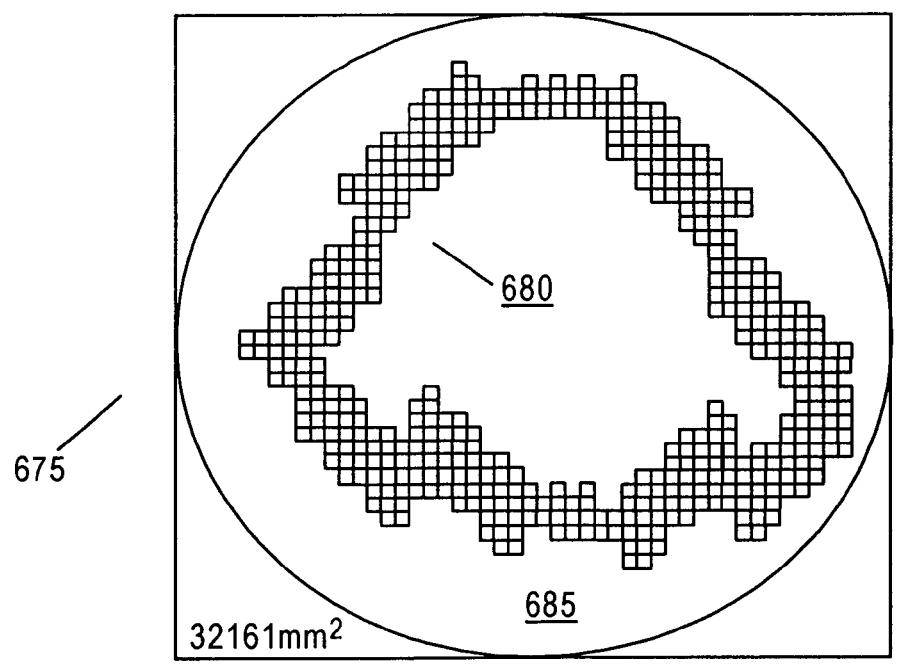

Examples of the residue maps, obtained from the comparison of the tested wafer maps to the reference wafer maps, are shown in FIGS. 6*b* through 6*d*. The numbers 610 shown on the bottom left corner of the residue maps provides a polishing quotient indicating a determined total defective areas of the wafer, such as under-polished or over-polished areas, but may also indicate that a defect (such as a scratch unpolished area on the wafer.

FIG. 6*a* shows a residue map 600 of a fully polished wafer 605, having no residue metal pixels. FIG. 6*b* shows a residue map 625 that has a limited number of pixels that are determined to be under-polished (and therefore containing some metallic residue) 630. However, the total area of under-polishing is deemed to be below a first threshold, and further re-polishing is therefore not required.

FIG. 6*c* shows a residue map 650 containing a number of additional pixels that are determined to be under-polished (and therefore containing some metallic residue 655. In this instance, the total area of under-polishing is deemed to be above a first threshold. Hence, the wafer is deemed to require additional polishing and is preferably returned to the CMP process for further polishing.

FIG. 6*d* shows a residue map 675 of a substantially over-polished wafer 685, containing many over-polished pixels 680.

The images in FIG. 6 confirmed that the inspection tool of FIG. 5 is capable of measuring the residue metal on polished wafers. Hence, it has the ability to replace the current visual inspection process that involves human visual inspection, defect map generation on an inspection tool and browsing on the wafer using a microscope. To further evaluate the residue metal detection application a repeatability test was performed.

Two wafers were selected from the available set of the test wafers, one fully polished and one under polished. Using the inspection tool, twenty scans were performed on each wafer and the collected data was analyzed using the methodology described earlier. The repeatability results for the determined metal residues are summarized in Table 3 below.

TABLE 3

Repeatability data on tungsten-deposited, polished test wafers

| | LT = 20 | | LT = 31 | |
|---|---|---|---|---|
| Scan# | Wafer#2 | Wafer#5 | Wafer#2 | Wafer#5 |
| 1 | 739 | 0 | 261 | 0 |
| 2 | 764 | 18 | 280 | 0 |
| 3 | 734 | 6 | 279 | 0 |
| 4 | 751 | 10 | 281 | 0 |
| 5 | 778 | 15 | 289 | 0 |
| 6 | 765 | 6 | 281 | 0 |
| 7 | 730 | 6 | 290 | 0 |
| 8 | 744 | 7 | 280 | 0 |
| 9 | 744 | 7 | 288 | 0 |
| 10 | 746 | 9 | 273 | 0 |
| 11 | 745 | 5 | 281 | 0 |
| 12 | 762 | 17 | 285 | 0 |
| 13 | 748 | 13 | 277 | 0 |
| 14 | 679 | 14 | 251 | 0 |
| 15 | 692 | 11 | 259 | 0 |
| 16 | 715 | 5 | 261 | 0 |
| 17 | 727 | 5 | 266 | 0 |
| 18 | 716 | 17 | 264 | 0 |
| 19 | 717 | 2 | 273 | 0 |
| 20 | 730 | 3 | 270 | 0 |
| AVG | 736.300 | 8.800 | 274.450 | 0.000 |
| STD | 24.381 | 5.327 | 11.052 | 0.000 |
| Repeatability | 0.967 | 0.395 | 0.960 | 100.000 |

At a given threshold (LT) value the inspection tool reports a particular amount (area (A)) of metal residue for the wafer. Each of the twenty (n) scans report a metal residue area (Ai) for the wafer. Hence, an average value for the accuracy of the repeatability tests may be calculated as:

$$AVG = \frac{\sum_i A_i}{n} \quad [20]$$

The standard deviation (STD) for this set of data is given as:

$$STD = \sqrt{\frac{n(\sum_i (A_i)^2) - \left(\sum_i A_i\right)^2}{n(n-1)}} \quad [21]$$

The repeatability for the given sample set is defined as:

$$R = \left(1 - \frac{STD}{AVG}\right) \quad [22]$$

The obtained repeatability data shows that for an under-polished wafer the residue area reported has a repeatability rating of approximately 96%. The preferred embodiment of the present invention uses a single threshold value. However, it is envisaged that further threshold values can be used to provide an indication of the varying degrees of polishing performance or subsequent actions to take with the scanned wafer, for example selective re-polishing. At a threshold value of LT=20 the residue metal detection analysis provides a significant number of false alarms on the fully polished wafer. It is noteworthy that at a threshold value of LT=31, the false alarms are eliminated. However, the residue area reported on wafer #2 is reduced from approximately 730 mm to 275 mm$^2$ when assessing the threshold values of LT=20 and LT=31 respectively.

The above measurements and analysis were performed on Tungsten deposited wafers. Similar tests were carried out on Copper (Cu) wafers, yielding similarly impressive results. Furthermore, similar repeatability tests were performed for copper wafers. Table 4 summarizes the data obtained on these Cu wafers.

TABLE 4

Repeatability data on Cu CMP test wafers.

| | LT = 20 | | LT = 28 | |
|---|---|---|---|---|
| Scan# | Wafer#7 | Wafer#8 | Wafer#7 | Wafer#8 |
| 1 | 4400 | 0 | 1991 | 0 |
| 2 | 4432 | 2 | 1979 | 0 |
| 3 | 5599 | 2 | 2091 | 0 |
| 4 | 4377 | 2 | 1995 | 0 |
| 5 | 4452 | 1 | 1989 | 0 |
| 6 | 4396 | 1 | 1986 | 0 |
| 7 | 4564 | 0 | 1999 | 0 |
| 8 | 4493 | 1 | 1996 | 0 |
| 9 | 4632 | 1 | 2006 | 0 |
| 10 | 4710 | 0 | 2016 | 0 |
| 11 | 4420 | 3 | 1992 | 0 |
| 12 | 4884 | 1 | 2023 | 0 |
| 13 | 4677 | 0 | 2013 | 0 |
| 14 | 4686 | 1 | 2008 | 0 |
| 15 | 4693 | 0 | 2016 | 0 |
| 16 | 4730 | 1 | 2006 | 0 |
| 17 | 4684 | 0 | 2012 | 0 |
| 18 | 4877 | 0 | 2004 | 0 |
| 19 | 5193 | 0 | 2055 | 0 |
| 20 | 4653 | 1 | 2003 | 0 |
| AVG | 4677.600 | 0.850 | 2009.000 | 0.000 |
| STD | 296.921 | 0.875 | 25.284 | 0.000 |
| Repeatability | 0.937 | −0.030 | 0.987 | 100.000 |

The results for Copper show a similar trend to that noticed in the Tungsten wafers. However, the number of false alarms on the fully polished copper wafer is much less at LT=20 than that of tungsten wafers. Hence, in the preferred embodiment of the present invention, the use of particular threshold values is made dependent upon the type of metalization used in the deposition process, to ensure acceptable correlation between the selected threshold value and a false alarm/capture rate.

It will be understood that the full-wafer post metal deposition and polishing inspection mechanism, as described above, is conveniently characterized by the following features: (i) The process is not limited to pre-defined inspection areas, but can be performed on a whole wafer. (ii) The inspection process may be performed in a single step. (iii) The inspection of wafers has negligible impact on the manufacturing/inspection cycle time and can therefore attain up to 100% sampling rate. (iv) Instant feedback to the CMP tool can be provided to adjust the polishing process, polishing locations or polishing time. (v) The process can be configured as a fully automated visual inspection process, and is not subject to the vagaries of human judgment. (vi) It is able to generate residue maps that can be scanned into a microscope/SEM Vision for a subsequent, thorough, review of the CMP process.(vii) It provides a higher resolution image of residue, for more accurate analysis.(viii) The inspection method is able to work with a variety of metalization layers, in particular post CMP residue metal on both tungsten and copper wafers. (ix) The inspection time (<20 sec) is very low.(x) The improved inspection and review process automatically provides a higher manufacturing yield.

Whilst the specific and preferred implementations of the embodiments of the present invention are described above, it is clear that one skilled in the art could readily apply variations and modifications of such inventive concepts.

Thus, an improved method and apparatus for wafer inspection in a post-CMP residual metal inspection has been described wherein the aforementioned disadvantages associated with prior art arrangements have been substantially alleviated.

We claim:

1. A method of inspecting a plurality of wafers in an optical inspection tool, the method comprising the steps of:
   generating a reference wafer;
   polishing said reference wafer in a chemical mechanical polishing process following a metal deposition process such that the reference wafer is representative of a fully polished wafer;
   scanning said polished reference wafer into an inspection tool prior to performing further processing on the reference wafer;
   generating a gray level map for said scanned reference wafer;
   performing a metal deposition process on a number of wafers;
   polishing said number of wafers after said metal deposition process in a chemical mechanical polishing process;
   scanning said polished number of wafers into an inspection tool prior to performing further processing on the wafers;
   generating a number of gray level maps for one or more of said scanned wafers;
   comparing said gray level map of said reference wafer with one or more gray level maps of said number of said scanned wafers,
   determining whether one or more wafers exhibits an acceptable polishing quality based on said comparison; and
   returning the wafer to a polishing process if said comparison step leads to a determination that said wafer is under-polished.

2. The method of inspecting a plurality of wafers in an optical inspection tool according to claim 1, wherein the step of determining includes determining whether a scanned wafer is under-polished by detecting a regional change in gray level in said step of comparing.

3. The method of inspecting a plurality of wafers in an optical inspection tool according to claim 1, wherein the step of determining includes identifying under-polished areas of said scanned wafer as having a different brightness than corresponding fully polished areas under an inspection process selected from the list consisting of bright field inspection, dark field inspection and gray field inspection.

4. The method of inspecting a plurality of wafers in an optical inspection tool according to claim 1, wherein the step of determining includes identifying over-polished wafers of said scanned wafer under an inspection process selected from the list consisting of bright field inspection, dark field inspection and gray field inspection.

5. The method of inspecting a plurality of wafers in an optical inspection tool according to claim 1, the method further comprising the step of:
   performing a moving average on the scanned measurements over a predetermined number of sequential pixels, thereby providing, for each pixel, an average value of the predetermined number of pixels preceding it; and/or
   performing a moving standard deviation on the scanned measurements over a predetermined number of sequential pixels, thereby providing, for each pixel, a moving standard deviation of the predetermined number of pixels preceding it.

6. The method of inspecting a plurality of wafers in an optical inspection tool according to claim 1, wherein the step of scanning includes scanning substantially all of a respective wafer for said number of wafers.

7. The method of inspecting a plurality of wafers in an optical inspection tool according to claim 1, wherein said step of polishing includes polishing said wafers in substantially concentric rings.

8. The method of inspecting a plurality of wafers in an optical inspection tool according to claim 1, wherein said number of wafers include any combination of bare wafers, patterned wafers, sawn wafers, whole wafers, multi-chip modules.

9. The method of inspecting a plurality of wafers in an optical inspection tool according to claim 1, wherein the step of scanning includes scanning using a variable test pattern to obtain a variety of scanned measurements.

10. The method of inspecting a plurality of wafers in an optical inspection tool according to claim 9, wherein the step of scanning using a variable test pattern includes scanning in a manner that provides a cross section of scanned measurements that change as a function of a vertical distance from a wafer layer.

11. The method of inspecting a plurality of wafers in an optical inspection tool according to claim 1, wherein said scanning step is performed by a series of detectors.

12. The method of inspecting a plurality of wafers in an optical inspection tool according to claim 11, wherein said step of comparing includes comparing gray level areas from a number of said detectors.

13. The method of inspecting a plurality of wafers in an optical inspection tool according to claim 1, the method further comprising the step of averaging values obtained from said step of scanning.

14. The method of inspecting a plurality of wafers in an optical inspection tool according to claim 13, wherein the step of averaging values is obtained from averaging values from all detectors used in said step of scanning.

15. The method of inspecting a plurality of wafers in an optical inspection tool according to claim 13, the method further comprising the step of normalizing said averaged values according to a number of detectors used in a scanning operation.

16. The method of inspecting a plurality of wafers in an optical inspection tool according to claim 13, the method further comprising the step of computing a standard deviation of the averaged values obtained from said step of scanning.

17. The method of inspecting a plurality of wafers in an optical inspection tool according to claim 1, wherein the method further includes the step of:
   generating an event comprising one or more of the following:
   X, Y coordinates of the scanned area,
   an average gray level of said scanned area,
   a standard deviation over a predetermined number of pixels.

18. The method of inspecting a plurality of wafers in an optical inspection tool according to claim 17, wherein the method further includes the steps of:
grouping pixels of said scanned wafer into one or more blocks of pixels; and
grouping pixels of said scanned reference wafer into one or more blocks of pixels;
wherein said step of comparing includes comparing said scanned reference wafer map to a said scanned wafer map on a block-by-block basis, in order to determine whether said block of pixels in said polished wafer is of an acceptable quality.

19. The method of inspecting a plurality of wafers in an optical inspection tool according to claim 18, the method further comprising the step of:
reporting to an inspection tool in a substantially real-time manner, in response to said step of comparing gray level maps, that a block of pixels may be considered as one of:
containing a metal residue;
an under-polished block of pixels;
an over-polished block of pixels; or
a fully polished block of pixels,
such that a polishing process can be adapted in response to said comparison in a substantially real-time manner.

20. The method of inspecting a plurality of wafers in an optical inspection tool according to claim 1, wherein the method further includes the step of:
generating a residual metal map from said step of comparing gray level maps, whereby any difference in the compared gray level maps indicates a measure of the residual metal present on the wafers.

21. The method of inspecting a plurality of wafers in an optical inspection tool according to claim 20, the method further comprising a step, preceding said step of generating a residual metal map, of:
cropping a number of scanned values, or
padding said number of scanned values.

22. The method of inspecting a plurality of wafers in an optical inspection tool according to claim 1, wherein the method further includes the step of:
defining at least one threshold value based on an analysis of said scanned reference wafer, such that determining a value above the threshold value for the scanned wafer is indicative of a suspected wafer being either over-polished, under-polished or defective.

23. The method of inspecting a plurality of wafers in an optical inspection tool according to claim 22, wherein said at least one threshold value is pre-determined for a particular wafer or semiconductor product.

24. The method of inspecting a plurality of wafers in an optical inspection tool according to claim 22, wherein said at least one threshold value is programmed into a computer to be used in said determination step.

25. The method of inspecting a plurality of wafers in an optical inspection tool according to claim 22, the method further comprising the step of:
varying said at least one threshold value dependent upon a type of metalization used in said metal deposition process, to obtain an acceptable correlation between the selected threshold value(s) and a false alarm/capture rate.

26. A method of inspecting a plurality of wafers in an optical inspection tool, the method comprising the steps of:
generating a reference wafer;
polishing said reference wafer in a chemical mechanical polishing process following a metal deposition process such that the reference wafer is representative of a fully polished wafer;
scanning said reference wafer into an inspection tool;
generating a gray level map for said scanned reference wafer;
performing a metal deposition process on a number of wafers;
polishing said number of wafers after said metal deposition process in a chemical mechanical polishing process, wherein said step of polishing includes polishing said wafers in substantially concentric rings;
scanning said number of wafers into an inspection tool;
generating a number of gray level maps for one or more of said scanned wafers;
comparing said gray level map of said reference wafer with one or more gray level maps of said number of said scanned wafers;
determining whether one or more wafers exhibits an acceptable polishing quality based on said comparison; and
reporting said quality determination to a polishing tool in a substantially real-time manner, such that, upon determining a location of an under-polished wafer, a polishing process selects particular rings, out of a set of rings, to be used by the polishing tool in a re-polishing process.

27. A method for determining a quality of a polishing process applied to a metal deposited wafer, the method comprising the steps of:
polishing a wafer after a metal deposition process using a chemical mechanical polishing process;
scanning said polished wafer into an inspection tool, prior to performing further processing on the wafer, to create a wafer map;
grouping pixels of said scanned wafer into one or more blocks of pixels;
scanning a fully polished reference wafer into said inspection tool, prior to performing further processing on the reference wafer, to create a reference wafer map;
grouping pixels of said scanned reference wafer into one or more blocks of pixels; comparing said scanned reference wafer map to a said scanned wafer map on a block-by-block basis;
classifying one or more of said blocks as being either a block of pixels representing a defect in said wafer or a block of pixels representing a fully polished block of pixels, in order to determine whether said polished wafer is of an acceptable quality; and
returning the wafer to the polishing process if said comparison step leads to a determination that said wafer is under-polished.

28. The method for determining a quality of polishing of a metal deposited wafer according to claim 27, the method further comprising the step of:
calculating a total number of blocks determined as being defective;
comparing said number of blocks with one or more threshold values; and
determining whether said wafer is fully polished, over polished or under polished based on said comparison.

29. An inspection tool comprising:
an optical head for scanning a reference wafer that has been polished in a chemical mechanical polishing process following a metal deposition process such that the reference wafer is representative of a fully polished wafer, and for scanning a number of wafers that have been polished in a chemical mechanical polishing process following a metal deposition process; and a processor configured for generating a gray level map for said scanned reference wafer, for generating a number of gray level maps for one or more of said scanned wafers, for comparing said gray level map of said reference wafer with one or more gray level maps of said number of said scanned wafers, for determining whether one or more wafers exhibits an acceptable polishing quality based on said comparison, and for returning the one or more wafers to the polishing process if said comparison leads to a determination that the one or more wafers is under-polished.

30. A storage medium storing processor-implementable instructions and/or data for controlling a processor to carry out the steps of:

generating a gray level map for a scanned reference wafer that has been polished in a chemical mechanical polishing process following a metal deposition process, the reference wafer being scanned after polishing and prior to performing further processing on the reference wafer, such that the reference wafer is representative of a fully polished wafer;

generating a number of gray level maps for one or more of a number of scanned wafers that have been polished in a chemical mechanical polishing process following a metal deposition process, the wafers being scanned after polishing and prior to performing further processing on the wafers;

comparing said gray level map of said reference wafer with one or more gray level maps of said number of said scanned wafers;

determining whether one or more wafers exhibits an acceptable polishing quality based on said comparison; and returning the one or more wafers to the polishing process if said comparison step leads to a determination that said one or more wafers is under-polished.

31. The storage medium storing processor-implementable instructions and/or data according to claim 30, wherein the processor-implementable instructions and/or data includes any of the following:

(i) an inspection algorithm to control a scanning step;
(ii) an inspection algorithm to control a comparison step;
(iii) a wafer map, wherein the wafer map is:
  (a) a reference wafer map,
  (b) a wafer map to be inspected, or
  (c) a residual metal wafer map,
(iv) a threshold value for use in determining a quality of a scanned wafer, for example whether said scanned wafer is acceptable, under-polished, or deemed defective, or
(v) information relating to a product, a wafer type or layer of wafer that is being inspected.

32. An optical inspection apparatus for inspecting a plurality of wafers, the apparatus comprising:

means for receiving a number of metalized wafers polished in a chemical mechanical polishing process;

an optical head, operably coupled to the means for receiving, including a plurality of optical detectors for scanning said number of polished wafers, including at least one fully-polished reference wafer, prior to performing further processing on the wafers;

a processor, operably coupled to said optical head, for receiving and processing scanning information from said optical head, wherein said scanning information corresponds to said fully-polished reference wafer and one or more polished wafers; and a memory element, operably coupled to said processor for storing said scanning information relating to said fully polished reference wafer;

wherein said processor generates a gray level map for said fully-polished reference wafer and one or more polished wafers and compares said gray level map relating to said scanned fully-polished reference wafer to said gray level map relating to at least one scanned polished wafer to determine whether said at least one polished wafer exhibits an acceptable polishing quality based on said comparison, and returns the wafer to a polishing process if said comparison leads to a determination that said wafer is under-polished.

33. The optical inspection apparatus according to claim 32, wherein said processor determines whether a scanned wafer is under-polished by detecting a difference between the gray level map of the scanned full-polished reference wafer and the scanned polished wafer.

34. The optical inspection apparatus according to claim 32, wherein said processor applies a weighting function to measurements from said optical detectors to take into account an acceptability of determining metal residue at a particular location of a given wafer.

35. The optical inspection apparatus according to claim 32, wherein said processor generates a residual metal map from said comparison of said gray level maps, whereby any difference in the gray level in the compared gray level maps indicates a measure of the residual metal present on the wafers.

36. The optical inspection apparatus according to claim 32, wherein said processor defines at least one threshold value based on a type of metalization used in the deposition process applied to a particular wafer or semiconductor product, to obtain an acceptable correlation between the selected one or more threshold values and a false alarm/capture rate.

37. The optical inspection apparatus according to claim 32, wherein said optical detectors are arranged to enable scanning of substantially all of a respective wafer of said number of wafers.

38. The optical inspection apparatus according to claim 37, wherein said optical detectors are configured to scan said wafers in a variable test pattern to obtain a variety of scanned measurements.

39. The optical inspection apparatus according to claim 38, wherein said optical detectors are configured to scan in a manner that provides a cross section of scanned measurements that change as a function of a vertical distance from a wafer layer.

40. The optical inspection apparatus according to claim 32, wherein said processor groups pixels of said scanned wafer into one or more blocks of pixels, and groups pixels of said scanned reference wafer into one or more reference blocks of pixels, and said processor compares said scanned reference wafer map to a said scanned wafer map on a block-by-block basis, in order to determine whether said polished wafer is of an acceptable quality.

41. The optical inspection apparatus according to claim 40, wherein said processor reports back to a polishing tool in a substantially real-time manner, in response to comparing gray level maps, that one or more blocks of pixels may be considered as:

containing a metal residue;
an under-polished block of pixels;

an over-polished block of pixels; or a fully-polished block of pixels, such that a polishing process can be adapted in response to said comparison in a substantially real-time manner.

42. An inspection tool comprising:

an optical head for scanning a wafer that has been polished after a metal deposition process using a chemical mechanical polishing process and for scanning a fully polished reference wafer; and a processor configured for:

creating a reference wafer map of the reference wafer;

creating a wafer map of the scanned wafer;

grouping pixels of said scanned wafer into one or more blocks of pixels;

grouping pixels of said scanned reference wafer into one or more blocks of pixels;

comparing said scanned reference wafer map to a said scanned wafer map on a block-by-block basis;

classifying one or more of said blocks as being either a block of pixels representing a defect in said wafer or a block of pixels representing a fully polished block of pixels, in order to determine whether said polished wafer is of an acceptable quality; and returning the wafer to a polishing process if said classifying step leads to a determination that said wafer is under-polished.

43. A storage medium storing processor-implementable instructions and/or data for controlling a processor to carry out the steps of:

creating a wafer map of a scanned wafer that has been scanned after a polishing step and prior to performing further processing on the wafer;

grouping pixels of said scanned wafer into one or more blocks of pixels;

creating a reference wafer map of a fully polished scanned reference wafer that has been scanned after polishing and prior to performing further processing on the reference wafer;

grouping pixels of said scanned reference wafer into one or more blocks of pixels;

comparing said scanned reference wafer map to a said scanned wafer map on a block-by-block basis;

classifying one or more of said blocks as being either a block of pixels representing a defect in said wafer or a block of pixels representing a fully polished block of pixels, in order to determine whether said polished wafer is of an acceptable quality; and returning the wafer to a polishing process if said classifying step leads to a determination that said wafer is under-polished.

* * * * *